(12) United States Patent
Chen et al.

(10) Patent No.: US 10,603,688 B2
(45) Date of Patent: Mar. 31, 2020

(54) MICROTOME

(71) Applicant: The Chinese University of Hong Kong, Hong Kong (CN)

(72) Inventors: Shih-Chi Chen, Hong Kong (CN); Ji Wang, Hong Kong (CN); Chenglin Li, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 67 days.

(21) Appl. No.: 15/837,819

(22) Filed: Dec. 11, 2017

(65) Prior Publication Data

US 2019/0176194 A1 Jun. 13, 2019

(51) Int. Cl.
| | | |
|---|---|---|
| *B06B 1/04* | (2006.01) | |
| *B01L 9/00* | (2006.01) | |
| *B26D 7/08* | (2006.01) | |
| *G01N 1/06* | (2006.01) | |
| *B06B 3/00* | (2006.01) | |
| *G01N 1/28* | (2006.01) | |

(52) U.S. Cl.
CPC ............. *B06B 1/045* (2013.01); *B01L 9/52* (2013.01); *B06B 3/00* (2013.01); *B26D 7/086* (2013.01); *G01N 1/06* (2013.01); *G01N 2001/061* (2013.01); *G01N 2001/065* (2013.01); *G01N 2001/2873* (2013.01)

(58) Field of Classification Search
CPC .... B06B 1/045; B06B 1/10; G01N 2001/061; G01N 1/06; G01N 2001/065; B01L 9/52; G01M 2001/7873; B26B 1/045; B26D 7/086; B26D 1/0006; B26D 7/2614; B26D 3/085; B26F 1/3839; B26F 1/40; Y10T 83/04; Y10T 83/8765
USPC .............................. 83/657, 13, 440, 575, 601
See application file for complete search history.

(56) References Cited

U.S. PATENT DOCUMENTS

| | | | | |
|---|---|---|---|---|
| 3,342,076 A | * | 9/1967 | Bodine .................... | B06B 1/10 74/87 |
| 7,347,766 B2 | * | 3/2008 | Nitta ........................ | B24B 1/04 125/13.01 |
| 8,180,479 B2 | * | 5/2012 | Xu ........................... | B26D 5/20 700/160 |
| 2003/0025569 A1 | * | 2/2003 | Tiihonen ................... | H01P 7/10 333/17.1 |
| 2004/0099107 A1 | * | 5/2004 | Stein ....................... | B06B 1/045 83/13 |
| 2013/0152757 A1 | * | 6/2013 | Nakai .................. | B26D 1/0006 83/601 |
| 2018/0240774 A1 | * | 8/2018 | DeAngelis ............. | H01L 24/75 |

* cited by examiner

*Primary Examiner* — Ghassem Alie

(74) *Attorney, Agent, or Firm* — Leydig, Voit & Mayer, Ltd.

(57) ABSTRACT

The present application discloses a microtome. The microtome includes: a blade cutting a soft material in a first direction, the first direction being a feeding direction of the soft material; a blade holder holding the blade; an actuator providing a vibration in a second direction along a cutting edge of the blade; and a frequency-tunable resonator driven by the actuator into vibration and fixedly connected to the blade holder to transfer the vibration to the blade holder and the blade, the resonator having a tunable resonant frequency in the second direction.

15 Claims, 9 Drawing Sheets

MICROTOME

TECHNICAL FIELD

The present application relates generally to a microtome having an oscillating blade. More particularly, the present application relates to a microtome for the production of thin slices of soft materials, which are intended for microscopic inspection.

BACKGROUND

A microtome is a sectioning instrument that allows for the cutting of thin slices of biological samples, known as sections. Typical sectioned samples have a thickness ranging from a few microns to 100s of microns. As sections may be observed and examined in a microscope through transmitted light, thin and smooth sections are often desired. To work with soft materials, a vibrating blade microtome is often employed. The vibrating blade microtome, a variation of the basic microtome, are widely recognized as superior for cutting thick sections from non-embedded or fresh samples. When in operation, the blade oscillates in a direction transverse to the cutting direction, which the sample advances at a steady speed.

SUMMARY

According to an aspect of the present application, a microtome is provided. The microtome includes: a blade cutting a soft material in a first direction, the first direction being a feeding direction of the soft material; a blade holder holding the blade; an actuator providing a vibration in a second direction along a cutting edge of the blade; and a frequency-tunable resonator driven by the actuator into vibration and fixedly connected to the blade holder to transfer the vibration to the blade holder and the blade, the resonator having a tunable resonant frequency in the second direction.

According to embodiments of the present application, the vibration of the blade of the microtome can facilitate the sectioning of a soft material. According to the principle of the present application, the vibration of the blade at a relatively high frequency (e.g., 100 Hz-800 Hz) may improve the sectioning performance (flatness, section thickness and the like of the sectioned slices). However, when the actuator generates a vibration at a relatively high frequency, it is difficult to vibrate the blade with a sufficient amplitude unless a large power is applied to the actuator, which will lead to an unstable vibration. According to the present application, if the natural resonant frequency of the mechanism is tuned to be a desired value, the amplitude of the vibration will be amplified. With a tunable natural resonant frequency of the mechanism, a sufficient amplitude at a relatively high frequency can be generated (while blade motions of undesired directions are suppressed) for processing a specific soft material. The principle model of this will be described in detail below.

DETAILED DESCRIPTION OF EMBODIMENTS

Hereinafter, a detailed description of the present application will be given with reference to the appended drawings.

Figure 1:
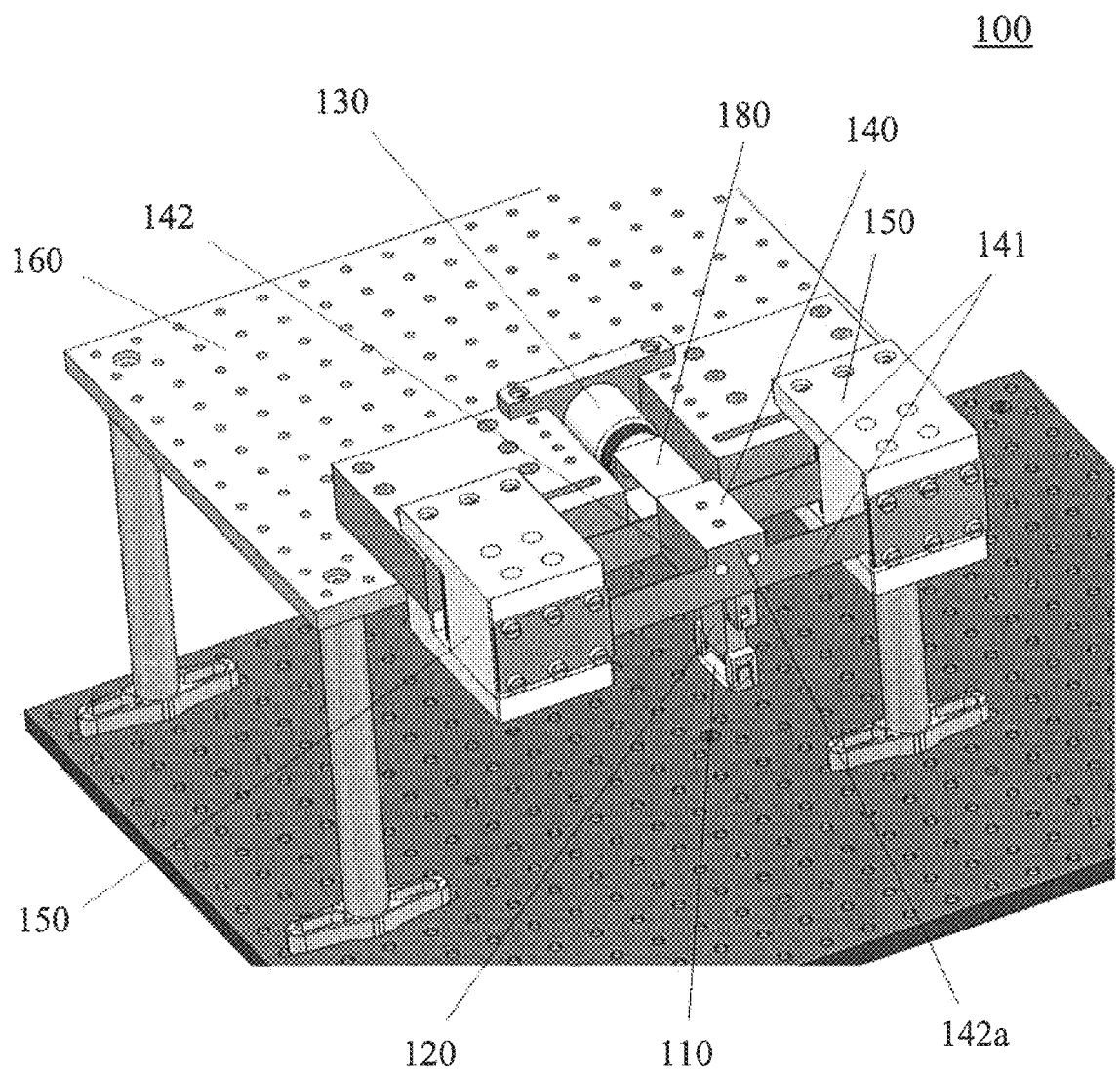
FIG. 1 is a schematic view of a microtome according to an embodiment of the present application.
Figure 2:
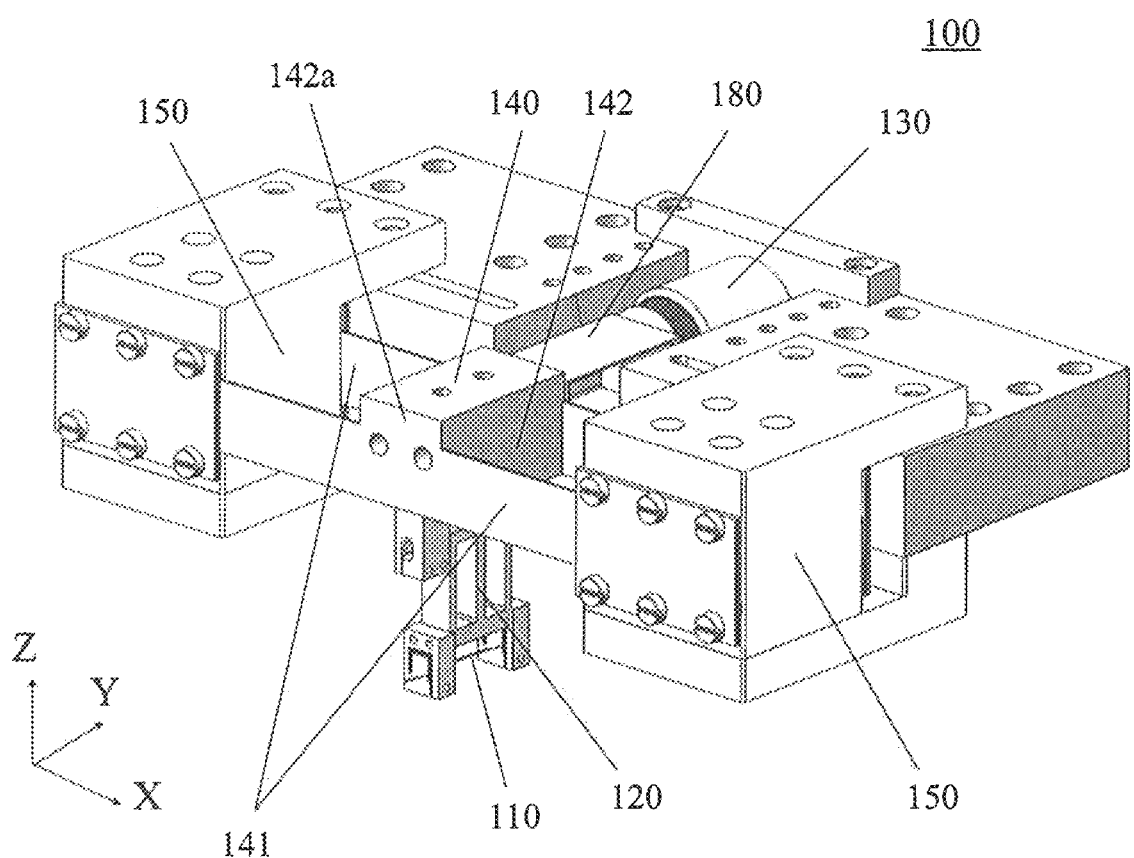
FIG. 2 is another schematic view of the microtome according to the embodiment of the present application.

FIG. 1 is a schematic view of a microtome according to an embodiment of the present application, and FIG. 2 is another schematic view of the microtome according to the embodiment of the present application.

As shown in FIGS. 1 and 2, the microtome 100 includes a blade 110, a blade holder 120, an actuator 130 and a frequency-tunable resonator 140. The blade 110 is arranged to cut a soft material (not shown in FIGS. 1 and 2). The soft material to be sectioned may be a soft tissue of a plant, animal or human being, for example, the brain, liver, or cornea, and may be fed in the X direction as shown in FIG. 2. The blade holder 120 is arranged to hold the blade 110. In an example, the blade holder 120 holds the blade 110 in an adjustable manner, which will be described in detail below.

The actuator 130 may provide a vibration in the Y direction (i.e. the direction along the cutting edge of the blade 110) as shown in FIG. 2, which may be any suitable actuator 130, e.g., a non-contact actuator, adapted to generate a linear vibration. For example, a voice coil motor may be used as the actuator 130. Under the actuation from the actuator 130, the frequency-tunable resonator 140 is driven into vibration. It can be understood that the driven frequency-tunable resonator 140 may have the same vibration frequency as the vibration generated by the actuator 130. The frequency-tunable resonator 140 is fixedly connected to the blade holder 120, and thus the vibration can be transferred from the actuator 130 to the blade holder 120 together with the blade 110, via the frequency-tunable resonator 140. Then, the blade 110 can vibrate in the Y direction, when cutting a soft material fed in the X direction.

The frequency-tunable resonator 140 has a tunable resonant frequency in the Y direction so that the resonant frequency of the combination of the resonator 140, the blade holder 120 and the blade 110 can be tuned to be a desired value for the purpose of the vibration with a suitable amplitude driven by the actuator 130.

The vibration of the blade of the microtome can facilitate the sectioning of a soft material. According to the principle of the present application, the vibration of the blade at a relatively high frequency (e.g., 100 Hz-800 Hz) may improve the sectioning performance (flatness, section thickness and the like of the sectioned slices). However, when the actuator generates a vibration at a relatively high frequency, it is difficult to vibrate the blade with a sufficient amplitude unless a large power is applied to the actuator, which will lead to an unstable vibration. According to the present application, if the natural resonant frequency of the mechanism is tuned to be a desired value, the amplitude of the vibration will be amplified. With a tunable natural resonant frequency of the mechanism, a sufficient amplitude at a relatively high frequency can be generated for processing a specific soft material. The principle model of this will be described in detail below.

Figure 3:
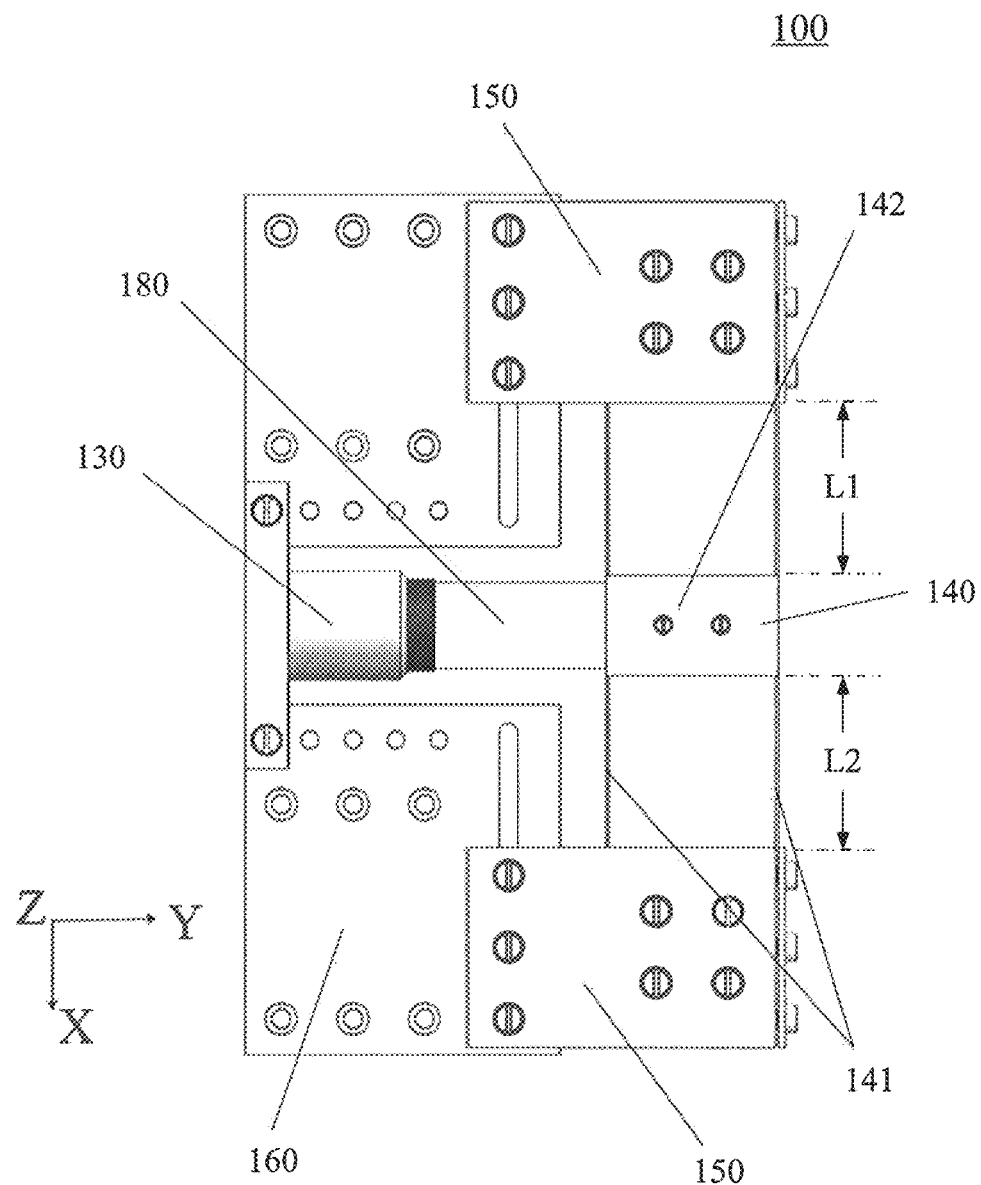
FIG. 3 is a top view of the microtome according to the embodiment of the present application.
Figure 4:
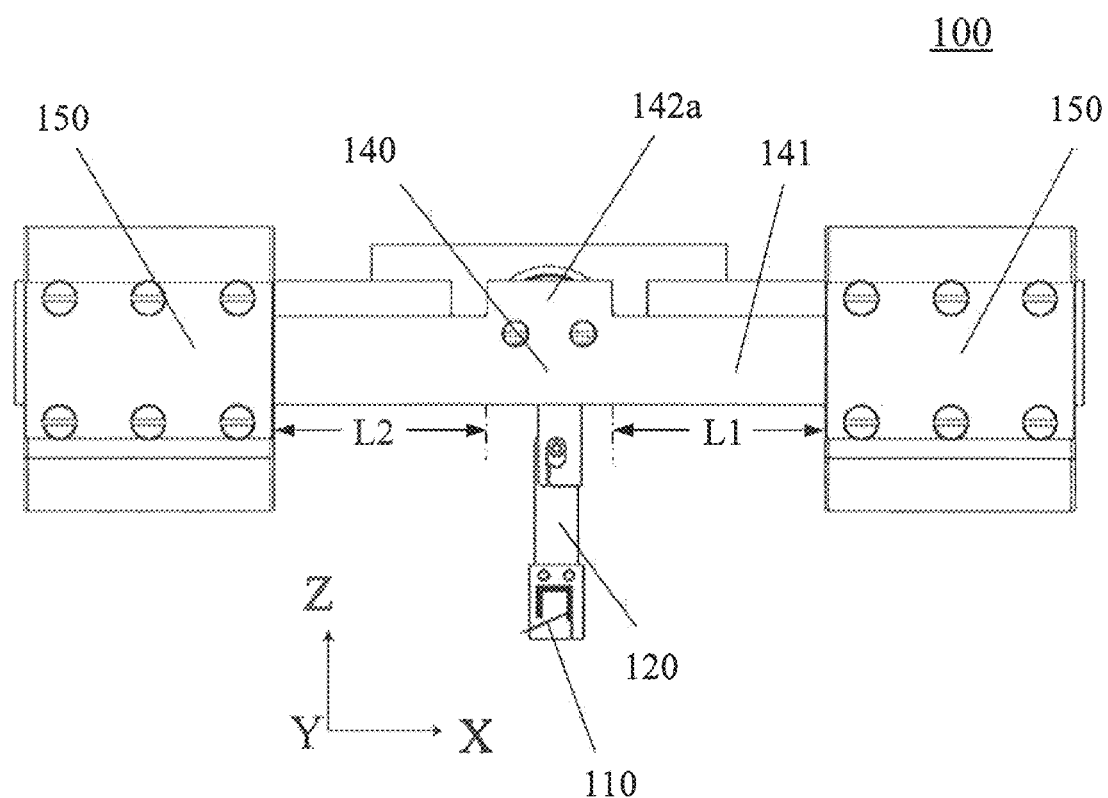
FIG. 4 is a front view of the microtome according to the embodiment of the present application.

FIG. 3 is a top view of the microtome according to the embodiment of the present application, and FIG. 4 is a front view of the microtome according to the embodiment of the present application.

The frequency-tunable resonator may include at least one beam extending in the X direction. As shown in FIGS. 1-4, the frequency-tunable resonator 140 includes two pairs of beams 141 and a central block 142. Each pair of the beams 141 includes two parallel beams symmetric with respect to the central block 142. Each of the beams 141 has an adjustable effective length L1 or L2 in the X direction, as shown in FIGS. 3 and 4. Before the vibration of the frequency-tunable resonator 140, one end of each beam 141 may be integral with (or fixed to) the central block 142, and the other end of the each beam 141 is fixed by a flexure holder 150 (which will be described in detail below). The effective length L1/L2 of the beam is the distance between the fix position at the flexure holder and the edge of the central block, as shown in FIGS. 3 and 4. Thus, the effective length L1/L2 of the beam can be adjusted by changing the fix position at the flexure holder. Then, the change of the effective length L1/L2 of the beam may result in a change of the natural resonant frequency of the frequency-tunable resonator.

In an example, the central block 142 is integral with the beam(s) 141, and the central block 142 and the beam(s) 141 are made of a metal. There is no moving part between the central block 142 and the beam(s) 141. Thus, there is no backlash within the frequency-tunable resonator 140, which has excellent wear characteristics.

An end of the central block 142 is aligned with the actuator 130, so that the frequency-tunable resonator 140 is driven by the actuator 130 into vibration. And, the central block 142 is fixedly connected to the blade holder 120. Thus, the frequency-tunable resonator 140 can vibrate together with the blade holder 120 and the blade 110.

According to an embodiment, each of the two pairs of parallel beams 141 is in a plate shape, as shown in FIGS. 1 and 2, so that the each beam 141 is flexible in the Y direction and stiff in the X and Z directions. Since the two ends of each beam 141 are fixed, the frequency-tunable resonator 140 can vibrate under the actuation of the actuator 130. The stiffness of the frequency-tunable resonator 140 in the Z direction can minimize its undesired out-of-plane wobbling in the Z direction, which may impact the performance of the sectioning and/or damage the microtome or soft material being sectioned.

The microtome 100 may further include a flexure holder. As shown in FIGS. 1 and 2, there are two pieces of flexure holders 150 at two sides of the frequency-tunable resonator 140, respectively. The flexure holders 150 are in a "C" shape and releasably clamp the beams 141 by using bolts or any other suitable mechanism. By changing the clamping position along the beam 141, the effective length L1 and L2 of the beam 141 can be adjusted.

The microtome 110 may further include a fixed platform 160, to which the flexure holder 150 is releasably fixed.

According to an embodiment, the actuator 130 is a non-contact linear actuator capable of providing the vibration with the frequency of 0-1000 Hz. In an example, the actuator 130 may provide the vibration with the frequency of 100-800 Hz. According to the present application, a vibration of the blade at a relatively high frequency (e.g., 100 Hz-800 Hz) may improve the sectioning performance. Given a specific soft material to be sectioned, the natural resonant frequency of the mechanism can be tuned to be a suitable value. Then, the actuator may provide a vibration with a frequency close to (but not equal to) the natural resonant frequency of the mechanism, so that the vibration of the mechanism can be amplified through the effect of mechanical resonance.

Figure 5:
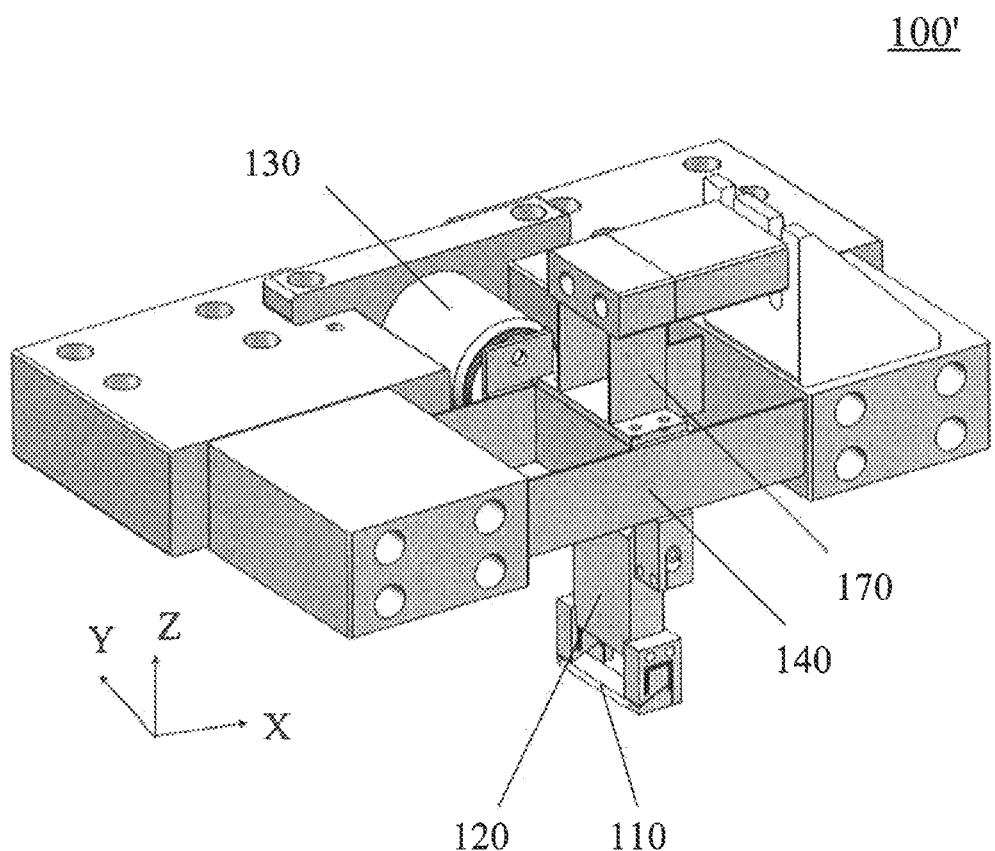
FIG. 5 is a schematic view of a microtome according to another embodiment of the present application.

FIG. 5 is a schematic view of a microtome according to another embodiment of the present application. As shown in FIG. 5, the microtome 100' further includes an additional flexure 170. The additional flexure 170 is attached to the resonator 140 to change the resonant frequency of the mechanism, i.e., the combination of the resonator 140 and the additional flexure 170, in the Y direction. In this embodiment, both ends of each beam 141 may be fixed, but the effective length of the whole beam system can be adjusted by changing the additional flexure 170 with different flexure length. To tune the natural resonant frequency of the mechanism, a suitable additional flexure can be attached to the resonator for sectioning a given soft material. Additional flexures with different flexure lengths may be suitable for the microtome to section different soft materials. As shown in FIG. 5, the additional flexure 170 extends in the Z direction.

Referring to FIGS. 1-3, the microtome 100 may further include a buffer component 180 between the actuator 130 and the frequency-tunable resonator 140. The buffer component 180 can transfer the vibration provided from the actuator 130 to the frequency-tunable resonator 140. With the buffer component 180, the undesired out-of-plane wobbling of the frequency-tunable resonator 140 in the Z direction can be further decreased.

Figure 6:
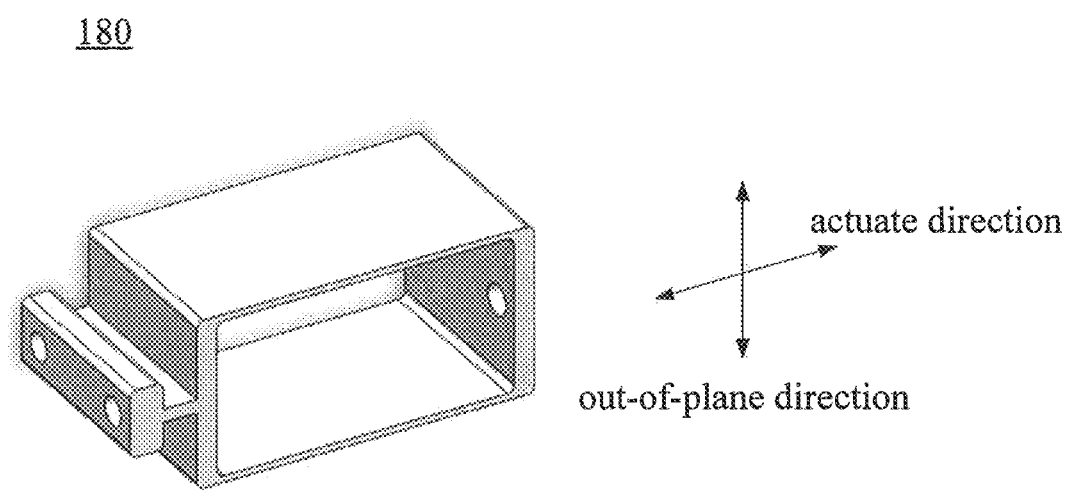
FIG. 6 is a schematic view of a parallelogram buffer component according to an example of the present application.

FIG. 6 is a schematic view of a parallelogram buffer component according to an example of the present application. As shown in FIG. 6, the buffer component may have a parallelogram cross section. Referring to FIGS. 1-3 and 6, two opposite sides of the parallelogram may be connected to the actuator 130 and the frequency-tunable resonator 140, respectively. Such a shape of the buffer component can diminish the undesired out-of-plane wobbling caused by manufacturing errors and/or assembly misalignments.

As shown in FIGS. 1, 2 and 4, the central block 142 may have a proof mass 142a extending above the beams 141. With the proof mass 142a, the center of mass of the frequency-tunable resonator 140 can be adjusted in the Z direction. For example, a suitable proof mass 142a may be designed so that the center of mass of the frequency-tunable resonator 140 can be merged with the center of stiffness of the frequency-tunable resonator 140.

Ideally, unwanted out-of-plane motion (in the Z direction) can be completely removed when the force transmitted from the actuator is simultaneously applied to the centers of mass and stiffness of the mechanism. According to some embodiments of the present application, the symmetric design of the frequency-tunable resonator 140 may ensure the force from the actuator 130 can be simultaneously applied to the merged centers of mass and stiffness of the mechanism. For example, the symmetric parallel beams 141 shifts the center of stiffness to the symmetric plane of the beams, merging with the center of mass. And, the proof mass 142a on the top of the blade holder and the blade allows the adjustment of the center of mass in the Z direction, merging with the center of stiffness.

Figure 7:
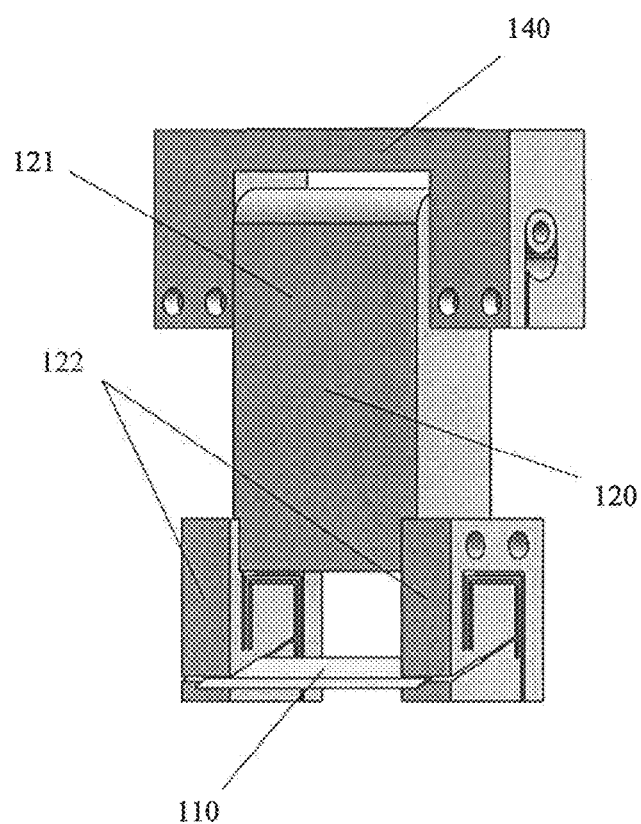
FIG. 7 is a schematic view of the assembly of the blade and the blade holder according to an embodiment of the present application.

FIG. 7 is a schematic view of the assembly of the blade and the blade holder according to an embodiment of the present application. As shown in FIG. 7, the blade holder 120 may include a body 121 and a pair of flexure clamps 122. The pair of flexure clamps 122 are fixedly connected to or integral with the body 121, and clamp the blade 110 in a tilt angle. The body 121 is fixedly connected to the frequency-tunable resonator 140 to ensure that the assembly of the blade 110 and the blade holder 120 can vibrate together with the frequency-tunable resonator 140. According to the soft material to be sectioned, the body 121 can be connected to the frequency-tunable resonator 140 at a suitable angle so that the blade 110 cuts the soft material at a suitable angle. That is, the connection angle of the body 121 relative to the frequency-tunable resonator 140 can be adjusted.

Figure 8:
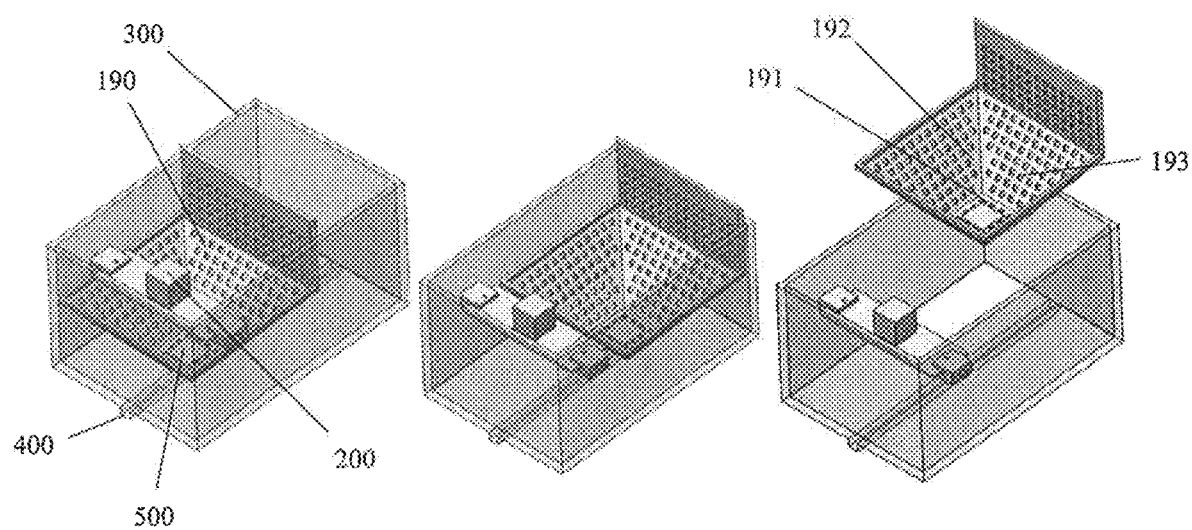
FIG. 8 shows a schematic view of three states of the material collector in the operation of the microtome according to the embodiment of the present application.

According to another embodiment of the present application, the microtome may further include a material collector for collecting and positioning the sectioned slices of the soft material. FIG. 8 shows a schematic view of three states of the material collector in the operation of the microtome according to the embodiment of the present application. During the sectioning of the soft material (the sample is a soft tissue in the embodiment), a sample 200 of the soft material is typically immersed in a biological buffering solution in a tank 300. The tank 300 may be driven by a linear stage 400 to feed the sample 200 to the vibrating blade (not shown in FIG. 8). When being cut off, a thin tissue slice floats/flows for a while in the solution and gradually sinks and lands on a random position at the bottom of the tank without the material collector. Conventionally, there is no effective way to collect the tissue slices, as the tissue slices are too thin and soft to handle. Directly picking the tissue slices up from the biological buffer solution via a tweezer will damage the slices.

As shown in FIG. 8, the material collector 190 has a shape of funnel to collect and position sectioned material slices 500 of a soft material. The funnel has a flat bottom 191 and an inclined wall 192. A plurality of holes 193 are arranged on the bottom 191 and the wall 192. As shown in the left of FIG. 8, the material collector 190 in the shape of a funnel is placed inside the buffer tank 300 during the blade cuts the soft material. After the soft material is sectioned, the funnel collects and aligns the slices 500 guided by the fluid flow induced by the array of holes 193 on the funnel, as shown in the middle of FIG. 8. Then, as shown in the right of FIG. 8, the funnel is removed out of the tank 300 and transferred to a tissue holder (not shown). Thus, the sectioned slices of the soft material can be effectively collected and positioned by using the material collector.

The microtome according to the present application can process soft material sectioning with unprecedented surface quality and flatness. This will significantly improve the imaging results for any microscopic and nanoscopic studies. In an example of the present application, the microtome is designed to achieve the specifications listed in the following Table 1.

TABLE 1

| Microtome Specifications according to an Example | |
|---|---|
| Feed rate | 0-15 mm/s |
| Vibration frequency | 0-800 Hz |
| Vibration amplitude | 0-2 mm |
| Section thickness | 10-200 μm |
| Parasitic Z-motion | <200 nm |
| Cutting characteristics | |
| Surface quality | 200 nm RMS |
| Defect rate | <1 defect in 1000 |

In addition, the microtome can be used to generate a 3-D resolved connectome (a connectome is a detailed wiring diagram of the entire brain, showing all the cells and their synaptic connections). The flat sectioning surface is critical to ensure synaptic connections can be mapped via different sectioned layers which cannot be achieved by conventional microtome models. The microtome will also be critical for improving the quality of the present 3-D two-photon tomography imaging technique.

Experimental results based on the present application have confirmed that a brain tissue can be sectioned into thin slices (10 s microns) with nanometer-level flatness by using the microtome of the present application, which is critical for 3D brain imaging and the creation of a brain connectome. According to the principle of the present application, a high cutting speed can harden the soft materials due to their viscoelastic properties and thus can enhance the sectioning outcome, making many unprocessable soft materials easy to cut.

The microtome development is driven by the better fundamental understanding of soft material cutting processes. From the study of the present application, it is theoretically and experimentally proved that the performance (flatness, section thickness etc.) of sectioning soft materials will be substantially improved when the sectioning is performed at high frequency, i.e., 300-800 Hz. The optimal cutting frequencies for different soft materials depend on their viscoelastic properties.

Figure 9:
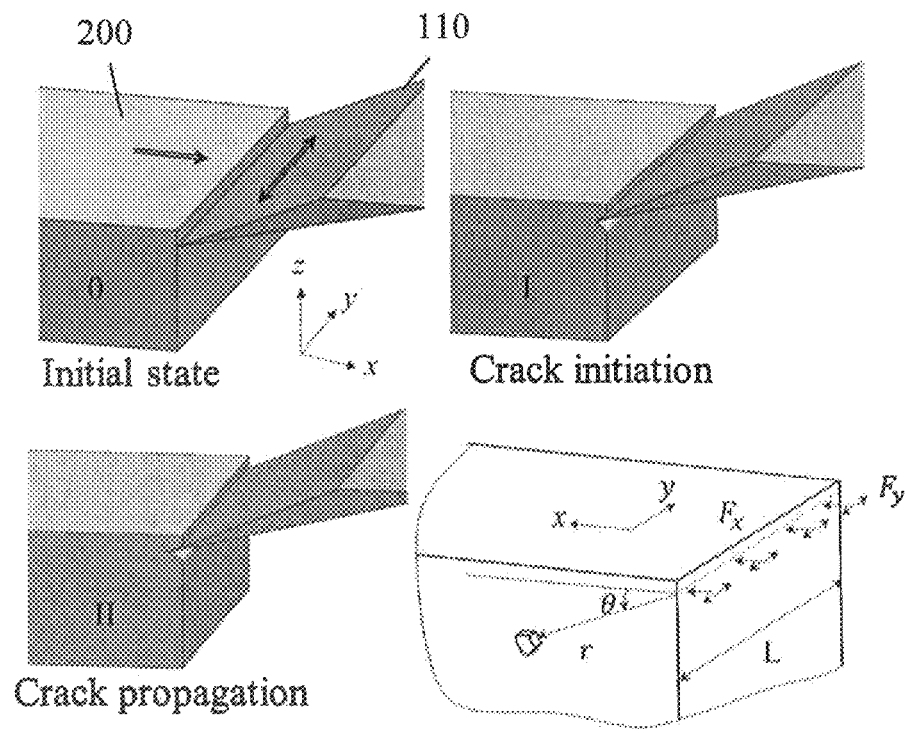
FIG. 9 illustrates different stages of soft material sectioning by using a vibrating blade as well as the schematic diagram of the loading condition at the beginning of soft material sectioning process.

FIG. 9 illustrates different stages of soft material sectioning by using a vibrating blade as well as the schematic diagram of the loading condition at the beginning of soft material sectioning process. To model the sectioning process, it can be assumed that the bottom of the soft material 200 is fixed on a stage that moves linearly towards the blade 110 at a constant speed. The blade 110 is in oscillation in a direction transverse to the feeding direction (shown in FIG. 9). The interaction forces between the blade 110 and the soft material 200 include normal cutting force $F_x$ and reciprocating shear cutting force $F_y$, which have the same frequency as the blade vibration. The relative motions between the blade 110 and the soft material 200 along y direction mostly involves sliding, and the shear force is thus considered as a friction force and can be written as $F_y=\mu F_x$. Previous studies on the contact characteristics of viscoelastic materials show that the friction coefficient between a soft material and a rigid surface depends on both the physical property of the contact interface and the sliding velocity. Here, the coefficient of friction is considered in the form of:

$$\mu = \nabla_z \frac{G_2(\omega')}{G^*(\omega')} \quad (1)$$

where $\nabla z$ describes the characteristics of the contact surface, which is a constant. $G_2(\omega')$ and $G^*(\omega')$ are the loss shear modulus and the complex shear modulus of the material under the characteristic frequency $\omega'=2A\omega/\pi r$, respectively. Given the blade vibrating displacement and vibrating velocity as: $Y=-A\cos\omega t$ and $Y'=A\omega\sin\omega t$, $F_y$ then can be written as:

$$F_y = F_y^* \sin \omega t \quad (2)$$

$$F_y^* = \nabla z \frac{G_2(\omega')}{G^*(\omega')} F_x$$

The soft material sectioning process can be divided into two stages, crack initiation and crack propagation. The stages 0, I and II in FIG. 9 show the initial state, the crack initiation and the crack propagation, respectively. At the stage of crack initiation, the material near the blade tip deforms under $F_x$ and $F_y$. Before the critical condition of the occurrence of the crack is met, $F_x$ keeps rising due to the continuous sample feeding, and the magnitude of $F_y$ increases with $F_x$ according to Eq. (2). At one point, the critical condition will be reached and the crack starts to propagate. This turning point between stages I and II can be observed from the curve of $F_x$ versus feeding distance, it is when normal cutting force $F_x$ reaches its peak value $F_{xmax}$, and causes the most material deformation during the cutting process.

At the stage of crack initiation, the material in the vicinity of the blade tip is in the state of line loading of a half space. This is because, comparing with the thickness of the cut off slice, the blade tip radius is much smaller, which makes stress concentrates sharply around the blade tip. By applying the theory of elastic contact mechanics and assuming the Poisson's ratio $v=0.5$, the stress and stress tensor can be analytically obtained under cylindrical coordinate system as:

$$\sigma = \begin{bmatrix} -\frac{2F_x \cos\theta}{\pi r L} & 0 & \frac{F_y}{\pi r L} \\ 0 & 0 & 0 \\ \frac{F_y}{\pi r L} & 0 & \frac{F_x \cos\theta}{\pi r L} \end{bmatrix} \quad (3)$$

$$\varepsilon = \begin{bmatrix} -\frac{F_x \cos\theta}{2G^*\pi r L} & 0 & \frac{F_y}{G^*\pi r L} \\ 0 & \frac{F_x \cos\theta}{2G^*\pi r L} & 0 \\ \frac{F_y}{G^*\pi r L} & 0 & 0 \end{bmatrix} \quad (4)$$

When under dynamic loading, the soft materials become hardened, so as the inner cohesive bond of the material. Experiments show critical fracture stress changes significantly with loading frequency. Thus, the maximum principle strain criterion is used here, instead of the maximum principle stress criterion, to determine the onset of crack. It is assumed that the critical maximum principle strain $\varepsilon_t$ does not change with dynamic loading. Given the radius of the blade tip as $r_0$, the maximum principle tensile stress $\varepsilon_1$ can be obtained from Eq. (5) as $\varepsilon_1 = F_y^*/G^*\pi r_0 L$, at the material surface when $\theta=\pi/2$. It should be noted that $\varepsilon_1$ is not directly related to the compressive force $F_x$. Because $F_y^*$ is determined by $F_x$, the crack onset state can be written as:

$$F_{x\,max} = \frac{\pi r_0 L \varepsilon_1 G^*(\omega)}{\nabla z G_2(\omega')/G^*(\omega')} \quad (5)$$

This solution shows that the initiation of crack results to low global material deformation when sectioning with high blade vibration frequency and amplitude. Eq. (5) also shows the critical crack onset state is not related to the sample feeding velocity. However, it is found in the experiments that $F_{xmax}$ changes when the feeding velocity is changed while other parameters remain the same. In fact, for soft materials, to make the crack propagate at a given velocity requires more energy than the threshold fracture energy required for breaking material bonds. Because soft materials are highly deformable, crack tip inside the material is surrounded by a relatively large energy dissipation area, the material within the area deforms dynamically as the crack propagates, and the energy dissipated in this area due to material viscoelasticity increases with the crack propagation velocity. In consideration of the effect of crack propagation velocity on the critical strain condition, the factor of viscoelastic dissipation $p(v)$ is introduced, and $\varepsilon_t$ is written as:

$$\varepsilon_t(v) = \varepsilon_0 p(v) \quad (6)$$

where $\varepsilon_0$ is the constant uniaxial tensile strain at failure, and when $v=0$, $\varepsilon_t(v)=\varepsilon_0$. Following the Persson model that $G(v)=G_0(1+v/v_0)^{1/3}$ ($G(v)$ is the energy per unit area required to propagate at the velocity of v, $G_0$ corresponds to extremely low value of v, and $v_0$ is the reference velocity) and considering that the function of strain energy is expressed as $U=\frac{1}{2}\varepsilon^T D\varepsilon$, without further demonstration, $p(v) = (1+v/v_0)^{1/6}$ can be written. The revised relation between maximum normal cutting force and sectioning parameters can be written as Eq. (7). Eq. (3) shows that the level of material deformation is determined by $F_x/G^*L$, and the quality of sectioning is determined by the level of material deformation. Therefore, $K=F_{xmax}/G'(\omega)$ is named the factor of sectioning quality, which can be written as Eq. (8). The smaller K is, the better the section quality is.

$$F_{x\,max} = \frac{\pi r_0 L \varepsilon_0 (1+v/v_0)^{1/6} G^*(\omega)}{\nabla z G_2(\omega')/G^*(\omega')} \quad (7)$$

$$K = \frac{F_{x\,max}}{F^*(\omega)L} = \frac{\pi r_0 \varepsilon_0 (1+v/v_0)^{1/6}}{\nabla z G_2(\omega')/G^*(\omega')} \quad (8)$$

Figure 10A:
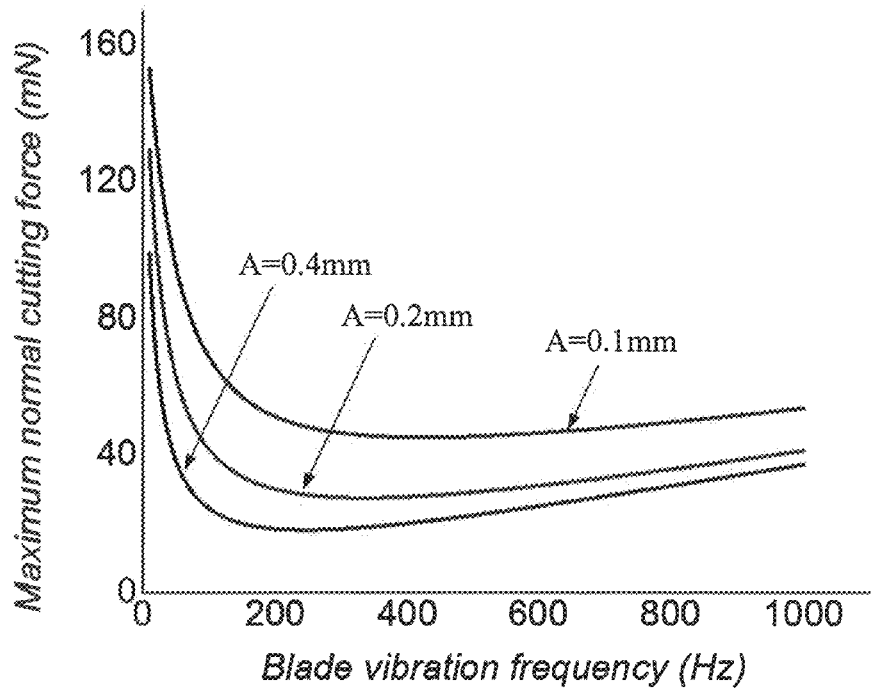
FIG. 10A shows the relation of maximum normal cutting force with blade vibration frequency.
Figure 10B:
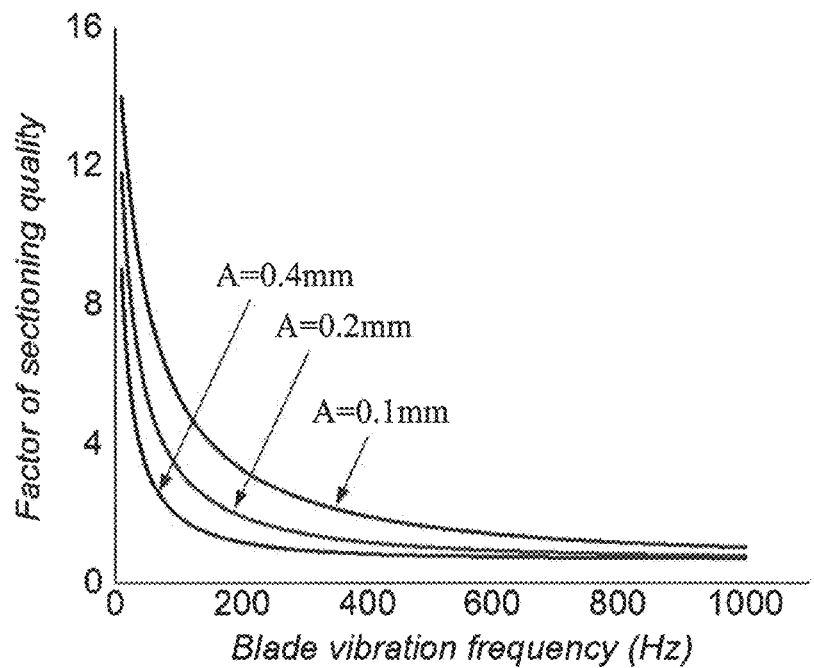
FIG. 10B shows the relation of the factor of sectioning quality with blade vibration frequency.

The physical property of soft materials has an obvious dependence on frequency under dynamic loading. For the example of 2% agarose gel, its complex shear modulus is expressed as:

$$G^*(\omega) = H\omega^\beta + jE\omega^\beta + jR\omega \quad (9)$$

where H=9.79 KPa, E=0.39 KPa, $\beta$=0.0254, R=0.0079 KPa. Substitute Eq. (9) into Eq. (8), the curve of the factor of sectioning quality K versus blade vibration frequency f=2$\pi\omega$ can be plotted in FIGS. 10A and 10B. FIG. 10A shows the relation of maximum normal cutting force with blade vibration frequency, and FIG. 10B shows the relation of the factor of sectioning quality with blade vibration frequency for 2% agarose gel under different blade vibration amplitude, where feeding velocity is 0.1 mm/s.

These analyses prove that small deformation and better sectioning can be achieved with high blade vibration frequency. Therefore, the microtome according to an embodiment of the present application may be designed to achieve such operating condition, i.e., a large range of tunable vibrating frequency (0-800 Hz) and vibrating amplitude (0-2 mm) for optimizing the cutting quality of different materials.

According to the microtome with a vast frequency tuning range is designed based on flexure structures driven by a linear actuator, e.g., voice coil motor (VCM). The flexure mechanism guides the blade holder so that the blade holder has only one degree of freedom, and the actuator generates linear reciprocating motion of the blade by outputting reciprocating force.

Below is the calculation for the mechanical model of the flexure-blade assembly system. Under the applied reciprocating force $F=F_0 \cos \omega t$, the dynamic equation of the system is given by:

$$y'' = 2\zeta\omega_0 y' + \omega_0^2 y = \frac{F_0 \omega_0^2 \cos \omega t}{k} \quad (10)$$

where m, k, $\omega_0=\sqrt{k/m}$, and $\zeta$ are the mass, stiffness, natural frequency, and damping ratio of the flexure-blade assembly system, $F_0$ and $\omega$ are the amplitude and frequency of the driving force, and y is the actual movement of the blade, which is given by the solution of Eq. (10):

$$y = A \cos(\omega t - \theta) \quad (11)$$

$$A = \frac{1}{\sqrt{(1-s^2)^2 + (2\zeta s)^2}} B \quad (12)$$

$$\theta = \arctan\frac{2\zeta s}{1-s^2} \quad (13)$$

where $s=\omega/\omega_0$, $B=F_0/k$ are the blade displacement responded to static excitement with the same amplitude.

Figure 11:
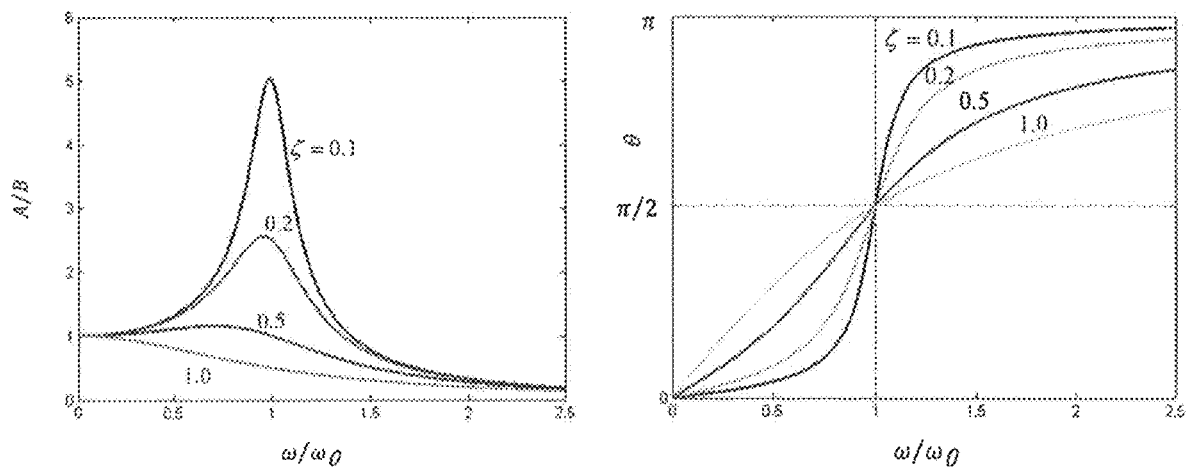
FIG. 11 presents the amplitude-frequency and phase-frequency characteristics.
Figure 12:
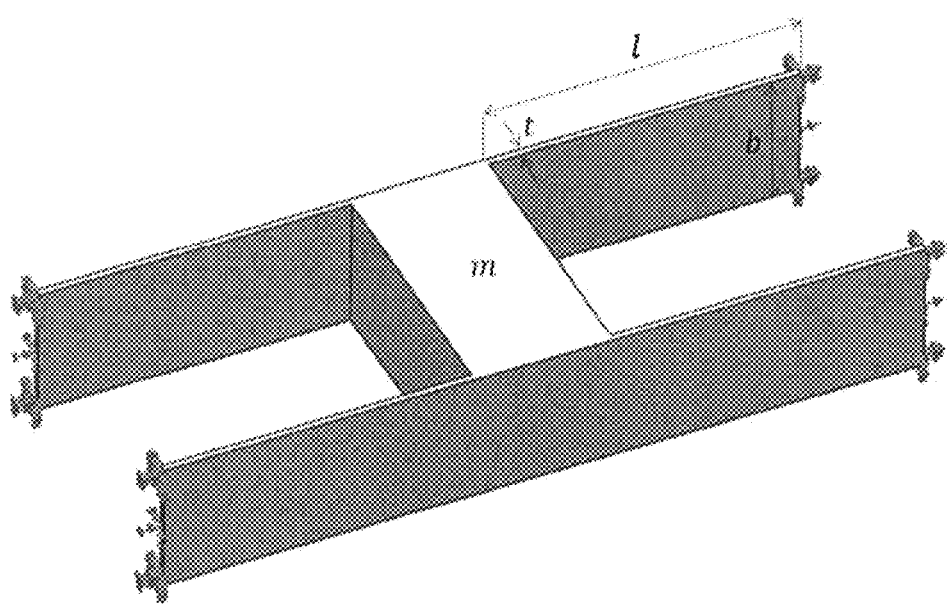
FIG. 12 is a schematic diagram of a four cantilever beams-mass system.

FIG. 11 presents the amplitude-frequency and phase-frequency characteristics. It can be seen that if the driving frequency is much higher than the system natural frequency $\omega_0$, the blade vibration amplitude approaches zero; and if the driving frequency is much lower than $\omega_0$, the blade vibration amplitude approaches static response $B=F_0/k$. It means that under the abovementioned two situations, to obtain enough blade vibration amplitude, the actuator needs to provide high enough power particularly when the system stiffness is high. However, by applying "mechanical resonance effect", i.e., driving the system in the range of [0.5 $\omega_0$, 1.5 $\omega_0$], the blade vibration amplitude can be easily amplified, with relatively low actuator output. However, a fixed $\omega_0$ cannot ensure the microtome has a large operation range. One way to address this matter is to design a frequency-tunable mechanism for adjusting the natural frequency of the flexure structure. FIG. 12 is a schematic diagram of a four cantilever beams-mass system. As shown in FIG. 12, this can be achieved by changing the beam length, where stiffness of the system is $k=Ebt^3/l^3$, and natural frequency is then given as $\omega_0=\sqrt{Ebt^3/ml^3}$. This result shows that by changing the beam length, the frequency tuning can be achieved in a large range.

Although the above descriptions include many specific arrangements and parameters, it should be noted that these specific arrangements and parameters only served to illustrate one embodiment of the present application. This should not be considered as the limitations on the scope of the application. It can be understood by those skilled in the art that various modifications, additions and substitutions may be made thereto without departing from the scope and spirit of the present application. Therefore, the scope of the present application should be construed on the basis of the appended claims.

What is claimed is:

1. A microtome comprising:
    a blade cutting a soft material in a first direction, the first direction being a feeding direction of the soft material;
    a blade holder holding the blade;
    an actuator providing a vibration in a second direction along a cutting edge of the blade; and
    a frequency-tunable resonator driven by the actuator into vibration and fixedly connected to the blade holder to transfer the vibration to the blade holder and the blade, the resonator having a tunable resonant frequency in the second direction;
    wherein the frequency-tunable resonator comprises:
    two pair of beams extending in the first direction and having an adjustable effective length in the first direction, wherein each of the two pair of beams is in a plate shape, and is flexible in the second direction and stiff in the first direction and a third direction perpendicular to the first and second directions.

2. The microtome of claim 1, wherein the frequency-tunable resonator further comprises:
    a central block integral with the beam and fixedly connected to the blade holder, an end of the central block being aligned with the actuator so that the frequency-tunable resonator is driven by the actuator into vibration.

3. The microtome of claim 2, wherein the two pairs of beams being parallel and symmetric with respect to the central block.

4. The microtome of claim 2, wherein the central block has a proof mass extending above the at least one beam so as to adjust a center of mass of the frequency-tunable resonator in a third direction perpendicular to the first and second directions to merge with a center of stiffness of the frequency-tunable resonator.

5. The microtome of claim 1, further comprising:
    a flexure holder releasably clamping the beam, and adjusting the effective length of the beam by changing a clamping position along the beam.

6. The microtome of claim 5, further comprising a platform, wherein the flexure holder is releasably fixed to the platform.

7. The microtome of claim 1, wherein the actuator is a non-contact linear actuator providing a vibration with a frequency of 0-1000 Hz.

8. The microtome of claim 7, wherein the actuator provides a vibration with a frequency of 100-800 Hz.

9. The microtome of claim 1, further comprising:
    an additional flexure attached to the frequency-tunable resonator to change the resonant frequency of a combination of the frequency-tunable resonator and the additional flexure in the second direction.

10. The microtome of claim 9, wherein the additional flexure extends in a third direction perpendicular to the first and second directions.

11. The microtome of claim 1, further comprising:
    a buffer component located between the actuator and the frequency-tunable resonator,
    transferring the vibration provided from the actuator to the frequency-tunable resonator, and decreasing out-of-plane wobbling of the frequency-tunable resonator in a third direction perpendicular to the first and second directions.

12. The microtome of claim 11, wherein the buffer component has a cross section of parallelogram, and two opposite sides of the parallelogram are connected to the actuator and the frequency-tunable resonator, respectively.

13. The microtome of claim 1, wherein the blade holder comprises:
  a body fixedly connected to the frequency-tunable resonator with an adjustable angle; and
  a pair of flexure clamps fixedly connected to the body or integral with the body, and clamping the blade in a tilt angle.

14. The microtome of claim 1, further comprising:
  a material collector having a shape of funnel to collect and position sectioned material slices.

15. The microtome of claim 14, wherein the funnel has a flat bottom and an inclined wall with a plurality of holes on the bottom and the wall.

* * * * *